United States Patent [19]

Sokolowski

[11] 4,412,993
[45] Nov. 1, 1983

[54] METHOD OF TREATING PSEUDOPREGNANCY, GALACTORRHEA AND MASTITIS IN MAMMALS

[75] Inventor: James H. Sokolowski, Kalamazoo, Mich.

[73] Assignee: The Upjohn Company, Kalamazoo, Mich.

[21] Appl. No.: 229,255

[22] Filed: Jan. 28, 1981

Related U.S. Application Data

[63] Continuation of Ser. No. 115,473, Jan. 25, 1980, abandoned.

[51] Int. Cl.³ ............................................. A61K 31/56
[52] U.S. Cl. ................................................... 424/243
[58] Field of Search ....................................... 424/243

[56] References Cited

U.S. PATENT DOCUMENTS 3,413,287  11/1968  Counsel et al. .............. 260/239.55
3,846,456  11/1974  Campbell et al. ............ 260/397.45

OTHER PUBLICATIONS

The Veterinary Record, vol. 76 (1964), No. 39, p. 1089, Article by Gerber et al.

Primary Examiner—Elbert L. Roberts
Attorney, Agent, or Firm—Sidney B. Williams, Jr.

[57] ABSTRACT

Prophylactic and therapeutic methods of treating pseudopregnancy and galactorrhea in mammals with 7α-methyltestosterones. Also, use of 7α-methyltestosterones in adjunct treatment of mastitis in mammals.

11 Claims, No Drawings

METHOD OF TREATING PSEUDOPREGNANCY, GALACTORRHEA AND MASTITIS IN MAMMALS

This is a continuation, of application Ser. No. 115,473, filed Jan. 25, 1980 now abandoned.

BACKGROUND OF THE INVENTION

1. Field of the Invention

This invention concerns the use of 7α-methyltestosterones in the treatment of pseudopregnancy, galactorrhea and mastitis in mammals. Pseudopregnancy (false pregnancy, pseudocyesis), galactorrhea and the need to terminate lactation are clinical problems often encountered by doctors and veterinarians. In the case of pseudopregnancy, the patient has milk, enlarged mammary glands and altered behavior patterns such as depression, or "grouchiness", and often self nursing. Although many cases of pseudopregnancy will undergo remission without treatment, the behavior changes are of concern and the stimulated mammary glands may be subject to mastitis. Therapeutic regimens now available often give uncertain response or take 4 to 8 days before an acceptable clinical response is observed. In addition, some existing treatment regimens often require retreatment because of recurrence of the condition after treatment is stopped.

2. Prior Art

Known methods for treating pseudopregnancy include testosterone injection, diethylstilbestrol injection or oral and megestrol acetate oral; Johnston, S. D., "Pseudopregnancy in Kirk R W" (ed), *Current Veterinary Therapy*, VI., p. 1240, Philadelphia, W. B. Saunders Co. (1977). The treatment of pseudopregnancy in dogs with testosterone propionate is also described by G. M. Spy, in "The Veterinary Record", Vol. 79, No. 10, p, 281 (1966). Gerber et al. describes the treatment of pseudopregnancy in dogs with 17α-methyl-19-nortestosterone (methyloestrenolone) in "The Veterinary Record", Vol. 76, No. 39, p. 1089 (1964). The relationship between prolactin levels and pseudopregnancy has been observed by several investigators. Smith et al., "Endocrinology", Vol. 98, No. 6, pp. 1370-77 (1976); Smith et al., "Serum Levels of Luteinizing Hormone and Progesterone During the Estrous Cycle, Pseudopregnancy and Pregnancy in the Dog", "Endocrinology", Vol. 94, pp. 404-412 (1974); Archer, D. F., "Current Concepts of Prolactin Philosophy in Normal and Abnormal Conditions", "Fertility and Sterility", Vol. 28, pp. 125-134 (1977); Hadley, J. F., "Uncongugated Oestrogen and Progesterone Concentrations in the Blood of Bitches with False Pregnancy and Pyometra", "The Veterinary Record", Vol. 96, pp. 545-547, (1975); Meites, J., "Neuroendocrinology of Lactation", "Journal of Investigational Dermatology", Vol. 63, pp. 119-124 (1974), discloses that the development of mammary glands in primates and rodents can be induced by combination of estrogen, progesterone, prolactin and growth hormone. Stoye, M., "Untersuchungen über die Möglichkeit pränataler and galaktogener Infektionen mit Ancylostoma caninum Ercolani 1859 (Ancylostomidae) biem Hund", "Zbl. Vet. Med.," B 20, pp. 1-39 (1973); and Knight, et al., "Serum Prolactin During Pregnancy and Lactation in the Beagle Bitch", "The Veterinary Record", Vol. 101, pp. 202-203 (1977) disclose that canine lactation can be stimulated and/or maintained by prolactin alone.

The therapeutic regimens now available for treating pseudopregnancy and/or galactorrhea often give uncertain response or take four to eight days before an acceptable clinical response is observed. In addition, some existing treatment regimens require retreatment because of recurrence of the condition after treatment is stopped. Compared to the prior art treatments, the treatment embodied in the instant invention is more effective, the response is more rapid and recurrence of the condition soon after therapy is minimized.

The 7α-methyl testosterones which are used in the methods of this invention are described in U.S. Pat. No. 3,341,557. Methods for preparing the 7α-methyltestosterones and a description of how they can be made into pharmaceutical compositions are also disclosed in said patent. The essential material constituting a disclosure of how to prepare the 7α-methyltestosterones and how to formulate them into pharmaceutical compositions is incorporated here by reference from U.S. Pat. No. 3,341,557.

SUMMARY OF THE INVENTION

This invention relates to the therapeutic or prophylactic use of 7α-methyltestosterones having the formula

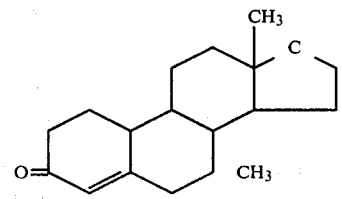

wherein C represents a group selected from the class consisting of

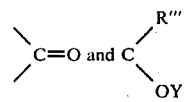

wherein R‴ is selected from the class consisting of hydrogen and a lower aliphatic hydrocarbon radical containing from 1 to 4 carbon atoms, inclusive, and Y is selected from the class consisting of hydrogen and the acyl radical of a hydrocarbon carboxylic acid containing from 1 to 12 carbon atoms, inclusive, for treatment of pseudopregnancy, galactorrhea in mammals, including humans, and to suppress milk flow as an adjunctive treatment in cases of mastitis.

A particularly effective compound is 7α-17-dimethyltestosterone (mibolerone), which has the formula

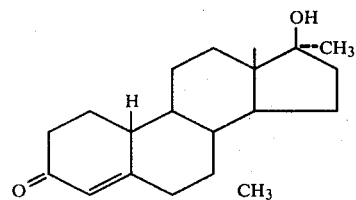

DETAILED DESCRIPTION OF THE INVENTION

The 7α-methyltestosterones can be used in mammals to treat pseudopregnancy, galactorrhea and to suppress milk flow in adjunctive treatment in cases of mastitis. These compounds can also be used prophylactically in preventing pseudo-pregnancy and galactorrhea.

The 7α-methyltestosterones prevent estrus and ovulation in dogs and cats. Since pseudopregnancy (pseudocyesism false pregnancy) and galactorrhea only occur after a bitch has expressed estrus and ovulated, then prevention of estrus is prophylactic for these post estrus conditions.

Other species, including rodents and man, have elevated serum prolactin levels associated with pseudopregnancy and galactorrhea. Although the mechanisms associated with initiation of pseudopregnancy are, at present, unknown, it is probable that prevention of the known secondary peak of serum estrogen also prevents prolactin release.

The 7α-methyltestosterones probably act therapeutically directly by blocking prolactin release and by tissue responses in the mammary glands. The suppression of psychic phenomena associated with pseudopregnancy is due to direct central nervous system effects of the 7α-methyltestosterones.

Prolactin is known to be associated with lactation stimulation and maintenance in several species including the dog. The prolactin suppressive effect of the 7α-methyltestosterones therefore results in lactation termination in cases of galactorrhea or where lactation termination is desirable following loss of offspring in the postparturient female. This latter effect would also prove useful in treating various types of mastitis where continued lactation activity would prevent or at least compromise completely successful therapy.

The 7α-methyltestosterones can be delivered orally by means of a treat, capsule, tablet, or liquid or parenterally by means of injection. Prophylactic dosage would be in the range of 0.1 to 250 micrograms per kg of body weight orally for various species (Example: bitch 0.1–10 mcg/kg; queen 5 to 500 mcg/kg) on a continuous daily basis. Therapeutic levels of 7α-methyltestosterones for pseudopregnancy and/or galactorrhea is in the range of 30 to 500 mcg/kg orally for up to 10 days.

As an adjunct to mastitis treatment the 7α-methyltestosterones can be used at levels of 30 to 500 mcg per kg orally for up to 30 days. Methods for formulating oral and parenteral dosage forms to provide the proper dosage are well known in the art and are applicable to preparing formulations that can be used in this invention. When used orally at the prescribed doses for 5 days, psychic changes associated with pseudopregnancy are eliminated in 12 to 36 hours and mammary glands are normal within 5 to 7 days.

There is generally no recurrence of the condition once treatment is stopped and there have been none of the side effects found with some other types of therapy.

The following examples are illustrative of the process of the present invention, but are not to be construed as limiting/

EXAMPLE 1

A solution of 7α,17-dimethyl-19-nortestosterone in propylene glycol was fed daily orally to female dogs at a dosage of from 0 to 360 mcg/10 kg. The dogs had the following history or clinical signs:

Presence of watery to thick, clear to brownish exudate or actual milk in the mammary glands. The mammary glands showed mild or severe enlargement and were, on occasion, painful when palpated. Other signs included: nest making, nursing inanimate objects, self-nursing, mental or personality changes, vomiting or diarrhea, anorexia or polyphagia and occasionally tenesmus as though in active labor. Response to treatment was evaluated on the first, second and fifth to seventh days after first treatment using the following terms and definitions:

| Treatment Response Evaluation Term | Definition |
|---|---|
| Excellent | Psychologically normal within 24 hours; mammary secretion ceased within 48–60 hours; mammary glands essentially normal 7 days after first treatment. |
| good | Psychologically normal within 24–36 hours; mammary secretion ceased within 72 hours; mammary glands essentially normal 7 days after first treatment. |
| fair | Psychologically normal in 36 to 48 hours; mammary secretion ceased within 5 days; mammary glands still enlarged 7 days after treatment started. |
| poor | Psychologically normal in 48 to 72 hours; slight mammary secretion and enlargement still evident 7 days after treatment started. |
| failure | No psychologically or physical response within 72 hours after first treatment. |

Dosages of 180 and 360 mg per 10 kg daily for 5 days generally resulted in good response rate and did not require retreatment after dosage was stopped. In some cases where the dosage was from 1 to 90 mcg daily, repeat treatment was required.

Examples of other 7α-methyltestosterones that can be used in the method of this invention are 7α-methyl-19-nortestosterone acetate
7α-methyl-19-nortestosterone
7α-methyl-19-nor-Δ4-androstene-3,17-dione
7α-methyl-17α-ethyl-19-nortestosterone
7α-methyl-17α-ethinyl-19-nortestosterone
7α-methyl-17α-ethinyl-19-nortestosterone 17-acetate.

I claim:

1. A method for treating a mammal suffering from a disease selected from the group consisting of pseudopregnancy and galactorrhea which comprises treating said mammal with 30–500 mcg/kg of a compound having the formula

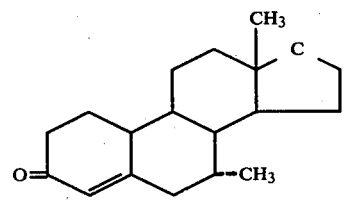

wherein C represents a group selected from the class consisting of

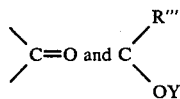

wherein R''' is selected from the class consisting of hydrogen and a lower aliphatic hydrocarbon radical containing from 1 to 4 carbon atoms, inclusive, and Y is selected from the class consisting of hydrogen and the acyl radical of a hydrocarbon carboxylic acid containing from 1 to 12 carbon atoms, inclusive.

2. A method according to claim 1 wherein the compound used is 7α-17-dimethyl-19-nortestosterone.

3. A method according to claim 2 wherein the mammal treated is suffering from pseudopregnancy.

4. A method according to claim 2 wherein the mammal treated is suffering from galactorrhea.

5. A method for the prevention of a pseudopregnancy or galactorrhea in a mammal that is susceptible to said disease which comprises treating said mammal with 0.1 to 250 mcg/kg of a compound having the formula

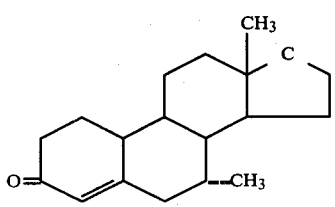

wherein C represents a group selected from the class consisting of

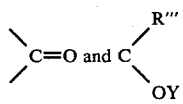

wherein R''' is selected from the class consisting of hydrogen and a lower aliphatic hydrocarbon radical containing from 1 to 4 carbon atoms, inclusive, and Y is selected from the class consisting of hydrogen and the acyl radical of a hydrocarbon carboxylic acid containing from 1 to 12 carbon atoms, inclusive.

6. A method according to claim 5 wherein the compound used is 7α-17-dimethyl-19-nortestosterone.

7. A method according to claim 5 or 6 wherein the disease to be prevented is pseudopregnancy.

8. A method according to claim 5 or 6 wherein the disease to be prevented is galactorrhea.

9. A method of suppressing lactation in mammal which comprises treating said mammal with 20 to 500 mcg/kg of a compound having the formula

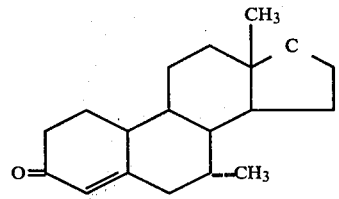

wherein C represents a group selected from the class consisting of

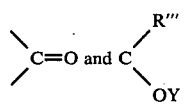

wherein R''' is selected from the class consisting of hydrogen and a lower aliphatic hydrocarbon radical containing from 1 to 4 carbon atoms, inclusive, and Y is selected from the class consisting of hydrogen and the acyl radical of a hydrocarbon carboxylic acid containing from 1 to 12 carbon atoms, inclusive.

10. An adjunct procedure to treating mastitis in a mammal which comprises treating said mammal with 30 to 500 mcg/kg of a compound having the formula

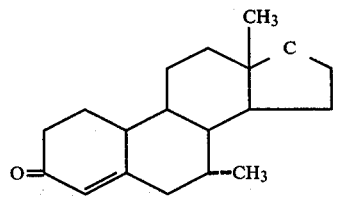

wherein C represents a group selected from the class consisting of

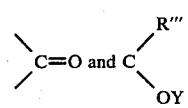

wherein R''' is selected from the class consisting of hydrogen and a lower aliphatic hydrocarbon radical containing from 1 to 4 carbon atoms, inclusive, and Y is selected from the class consisting of hydrogen and the acyl radical of a hydrocarbon carboxylic acid containing from 1 to 12 carbon atoms, inclusive.

11. An adjunct procedure according to claim 10 wherein the compound used is 7α-17-dimethyl-19-nortestosterone.

* * * * *